United States Patent [19]

Legal

[11] Patent Number: 5,086,767
[45] Date of Patent: Feb. 11, 1992

[54] VENTILATOR FOR ASSISTING THE BREATHING OF A PATIENT

[75] Inventor: Jules O. Legal, Manitoba, Canada

[73] Assignee: Canadian Aging & Rehabilitation Product Development Corporation, Winnipeg, Canada

[21] Appl. No.: 588,275

[22] Filed: Sep. 26, 1990

[51] Int. Cl.⁵ ............................................. A62B 00/00
[52] U.S. Cl. .......................... 128/205.18; 128/204.18; 128/205.11
[58] Field of Search ....................... 128/204.18, 205.11, 128/205.18; 417/43, 44, 480, 481; 92/125, 121, 120

[56] References Cited

U.S. PATENT DOCUMENTS

| | | | |
|---|---|---|---|
| 1,205,338 | 11/1916 | Farley | 417/482 |
| 1,404,116 | 1/1922 | Hafkesbrink | 417/482 |
| 2,468,272 | 4/1949 | Phillips | 92/125 |
| 3,658,443 | 4/1972 | Fumagalli | 128/204.18 |
| 3,916,889 | 11/1975 | Russell | 128/205.11 |
| 4,058,857 | 11/1977 | Runge et al. | 417/482 |
| 4,686,974 | 8/1987 | Sato et al. | 128/204.23 |

Primary Examiner—Edgar S. Burr
Assistant Examiner—Lisa E. Malvaso
Attorney, Agent, or Firm—Adrian D. Battison; Stanley G. Ade; Murray E. Thrift

[57] ABSTRACT

A ventilator for providing low pressure air for assisting the breathing of an imfirm patient includes a pump with a cylindrical chamber having a vane mounted within the chamber for sweeping the inside surface of the chamber in a pumping action. The pump is double-acting. Ports to the pump are located in a wedge-shaped divider member permanently mounted within the chamber and extending from the chamber to a shaft driving the vane. Valves for the ducts extending from the ports to respective inlets and outlets are mounted exteriorly of the wedge-shaped dividing member. The pump can therefore have lower volume and the shaft is directly driven providing high efficiency and simple adjustment of the volume supplied to the patient.

1 Claim, 4 Drawing Sheets

VENTILATOR FOR ASSISTING THE BREATHING OF A PATIENT

BACKGROUND OF THE INVENTION

This invention relates to a ventilator for assisting the breathing of a patient who may be paralyzed or sufficiently feeble of muscular strength to require assistance in the breathing action by the generation of pressure in the air flow passing into the patient to assist the inhaling action of the patient.

Ventilators are commonly provided for elderly, infirm or paralyzed patients to assist with breathing. In most cases the ventilator includes a pump for generating the necessary volume of air flow so that the air can be pressurized to be forced into the lungs of the patient during the inhaling action and released by the natural elasticity of the thoracic cavity of the patient in the exhaling action. Subsequent to the replacement of the "iron lung" system of the fiftys and sixties, ventilators have generally employed as a pumping system a reciprocating type pump with a cylindrical chamber and a piston moving axially of the chamber driven by a crank from a rotating shaft. The pump is usually designed to accommodate a maximum volume of air pumped of the order of four to four and a half liters which is the type of volume which would be drawn by a large person breathing vigorously. In order to supply a smaller volume to a smaller patient or a patient during relaxation, the throw of the crank is generally mechanically adjusted to reduce the stroke of movement of the piston within the cylinder.

A pump of this type is generally very heavy, mechanically complex, generates high friction and has high inertia. The pump is therefore suitable for a relatively unsophisticated unit which delivers a substantially fixed amount of air to the patient but cannot respond readily to changes in demand from the patient. In addition the unit is relatively large and heavy and requires a motor of relatively large power and hence the pump is unsuitable for a mobile unit to be driven by battery power.

SUMMARY OF THE INVENTION

It is one object of the present invention, therefore, to provide an improved ventilator and particularly an improved pump for use in a ventilator which overcomes many of the above disadvantages and hence enables the pump to be more suitable both for more accurate control of the volume of air to be supplied by the pump and also for a reduction in size and power requirement.

According to the invention, therefore, there is provided a ventilator for assisting the breathing of a patient comprising a pump for generating an air flow, inlet means for drawing air from an exterior supply into the pump, said inlet means including valve means for preventing expulsion of air through said inlet means from said pump, outlet means for communicating pumped air from the pump, a supply line for supplying air from the outlet means to the patient, valve means connected to the supply line operable to control supply of the air from the pump to the patient in an inhaling action and to allow release of air from the patient to the exterior in an exhaling action, a drive motor for the pump, the pump comprising a drive shaft, a housing defining a chamber having a chamber surface formed by a surface of revolution about a longitudinal axis of the drive shaft, a dividing member lying in an axial plane of the chamber and extending from the shaft to the peripheral wall, the inlet means including an inlet port communicating with the chamber at the dividing member and on one side of the dividing member, the outlet means including an outlet port communicating with the chamber at the dividing member and on said one side of the dividing member, a vane carried by the drive shaft and extending therefrom in a substantially axial plane, sealing means for sealing an edge of the vane relative to the chamber surface such that rotation of the drive shaft in a first angular direction through an angle less than 360° causes the vane to sweep around a portion of the chamber to draw air through the inlet port into the chamber and rotation in the opposed angular direction causes the vane to sweep around a volume of the chamber to cause the drawn air to be expelled through the outlet port to the patient.

According to a second aspect of the invention, therefore, there is provided a pump comprising a drive shaft, a housing defining a chamber having a chamber surface formed by a surface of revolution about a longitudinal axis of the drive shaft, a dividing member lying in an axial plane of the chamber and extending from the shaft to the peripheral wall, inlet means including an inlet port communicating with the chamber at the dividing member and on one side of the dividing member, outlet means including an outlet port communicating with the chamber at the dividing member and on said one side of the dividing member, a vane carried by the drive shaft and extending therefrom in a substantially axial plane, sealing means for sealing an edge of the vane relative to the chamber surface such that rotation of the drive shaft in a first angular direction through an angle less than 360° causes the vane to sweep around a portion of the chamber to draw air through the inlet port into the chamber and rotation in the opposed angular direction causes the vane to sweep around a volume of the chamber to cause the drawn air to be expelled through the outlet port.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

In the drawings like characters of reference indicate corresponding parts in the different figures.

DETAILED DESCRIPTION

Figure 1:
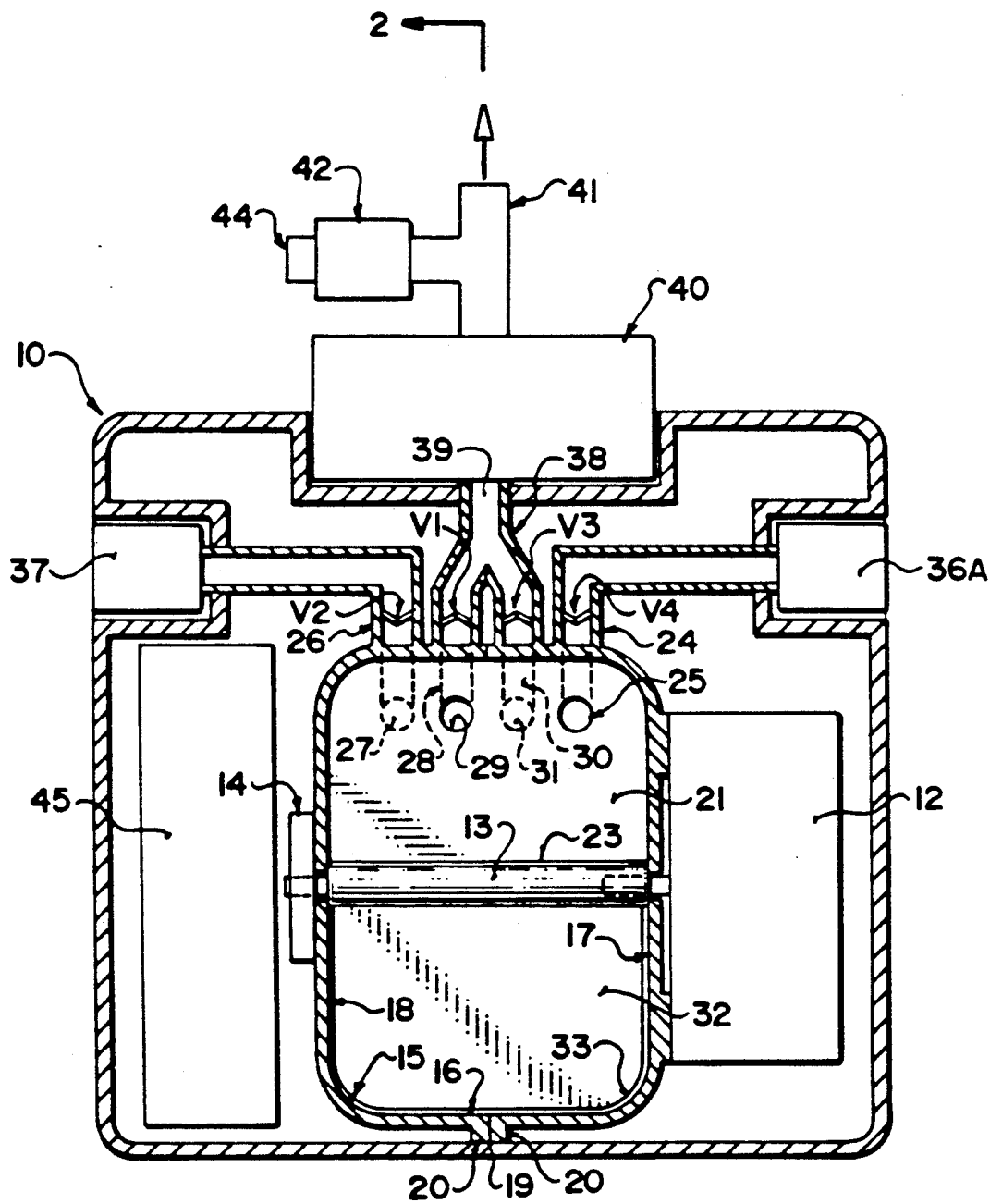
FIG. 1 is a schematic cross sectional view through a ventilator according to the present invention.
Figure 2:
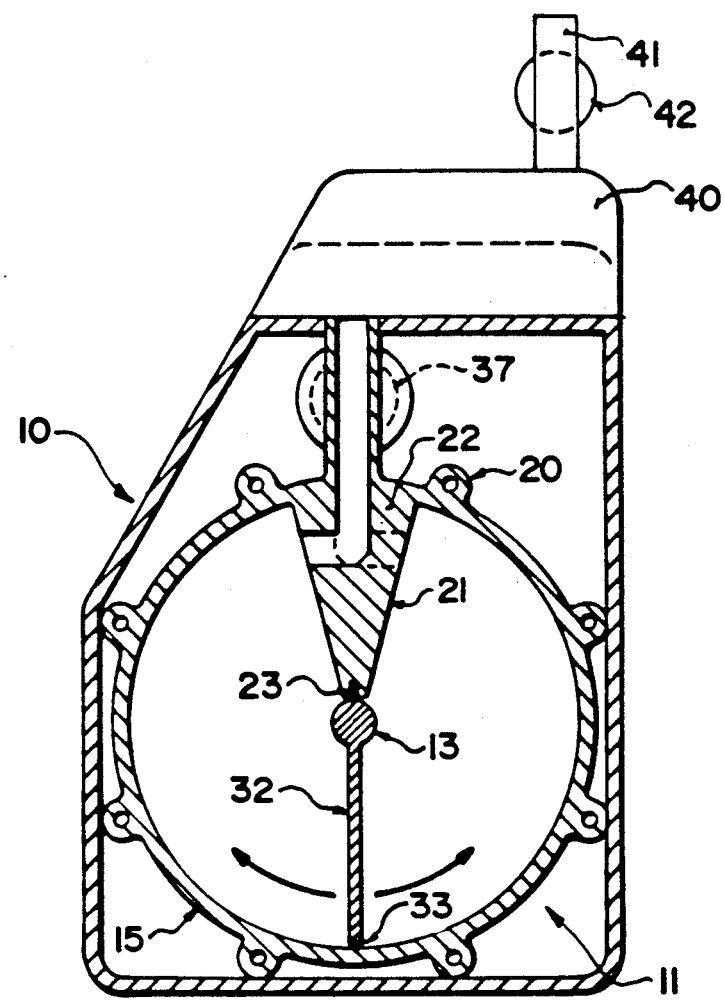
FIG. 2 is a cross sectional view along the lines 2—2 of FIG. 1.

A ventilator is shown in FIGS. 1 and 2 and comprises a housing 10 within which is mounted a pump 11 driven by a motor schematically indicated at 12.

The pump comprises a drive shaft 13 mounted in bearings 14 and rotatable about a substantially horizontal axis. In the embodiment shown, the motor 12 is mounted directly on the end of the drive shaft for communicating directly rotational movement to the shaft 13 for rotation about the longitudinal axis of the shaft.

The pump further includes a chamber 15 defined by a cylindrical peripheral wall 16 and end walls 17 and 18 with the end walls lying in radial planes of the axis spaced longitudinally of the axis so that the housing forms a substantially cylindrical hollow chamber surface coaxially surrounding the drive shaft 13 and formed as a surface of revolution around the axis of the shaft.

The housing is formed in two portions joined at a center line 19 by the clamping together of cooperating flanges 20 defined as a plurality of ears or lugs at spaced positions around the periphery of the housing.

Within the chamber is defined a wedge shaped manifold and divider 21 which is formed integrally with the wall of the chamber and extends from one end of the chamber along the shaft to the opposed end of the chamber and from an apex in contact with the shaft 13 to a base 22 where it is integrally formed with the wall. The wedge-shaped divider member is thus fixed inside the chamber and is not intended to be removed. A sealing member 23 is mounted in the apex of the dividing member at its position of contact with the shaft 13 so that the shaft can rotate while maintaining effectively a seal to prevent the passage of air between the shaft and the dividing member.

The dividing member 21 acts as a manifold for communication of air from a pair of inlets to a pair of outlets for cooperating in the pumping action. Specifically as best shown in FIG. 1, a first inlet duct 24 extends through the housing 10 to an inlet port 25 on one face of the dividing member. A second inlet duct 26 extends through the housing 10 into the dividing member 21 and terminates at a second inlet port 27 provided in the second face of the dividing member which is opposed to the face containing the port 25. Similarly a first outlet duct 28 extends through the dividing member and terminates at an outlet port 29 on the first face of the dividing member. A second outlet duct 30 extends to the dividing member and terminates at a second outlet port 31 on the second or opposed face of the dividing member.

Figure 3:
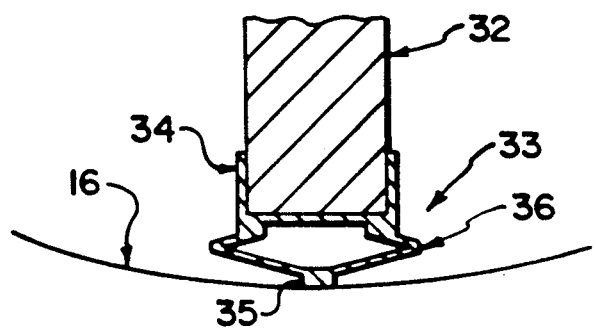
FIG. 3 is a cross sectional on an enlarged scale of the sealing arrangement at the edge of the vane.
Figure 4:
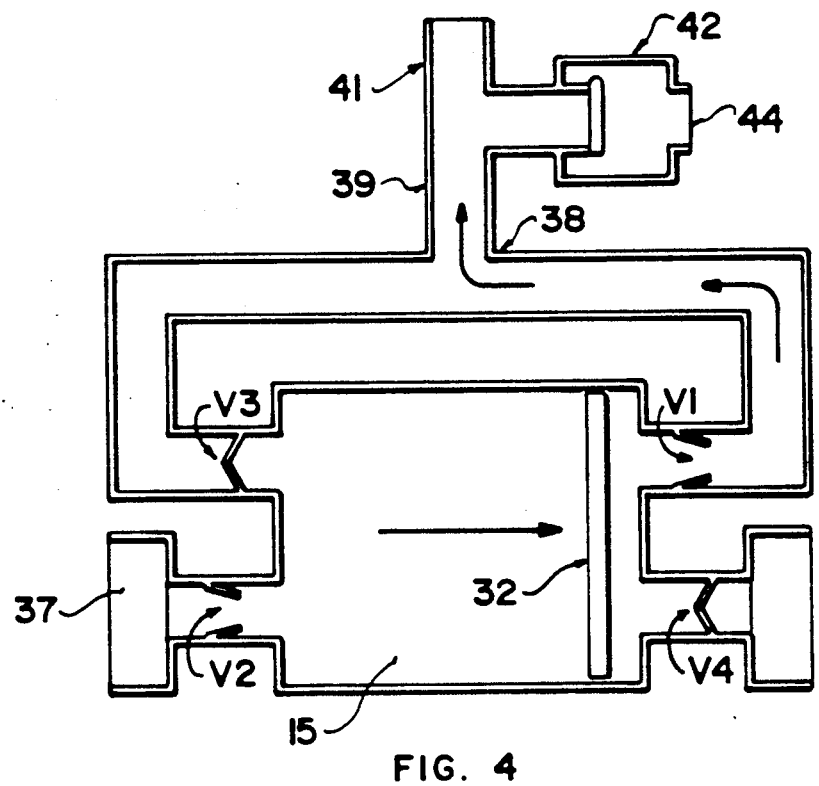
FIGS. 4, 5 and 6 are schematic illustrations showing sequential steps in the operation of the humidifier of FIG. 1.
Figure 5:
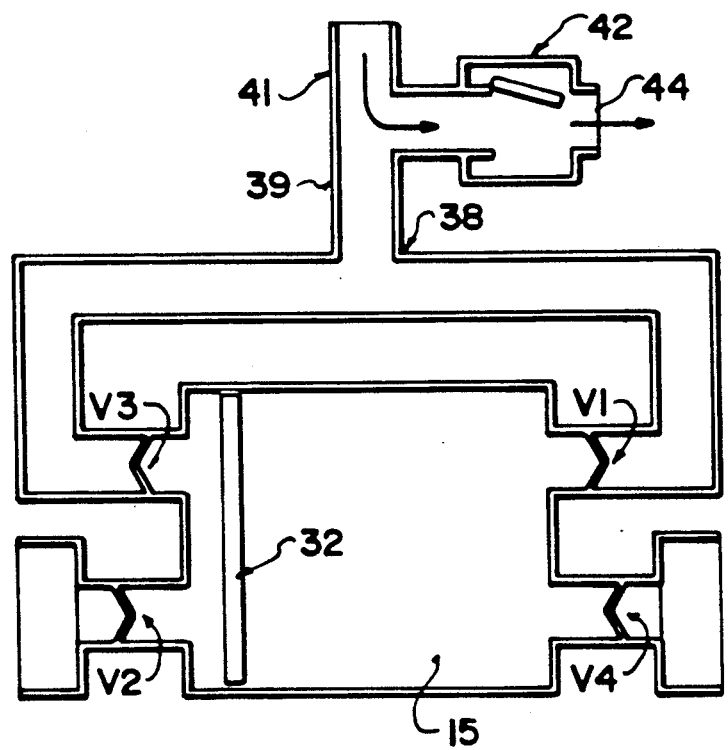
Figure 6:
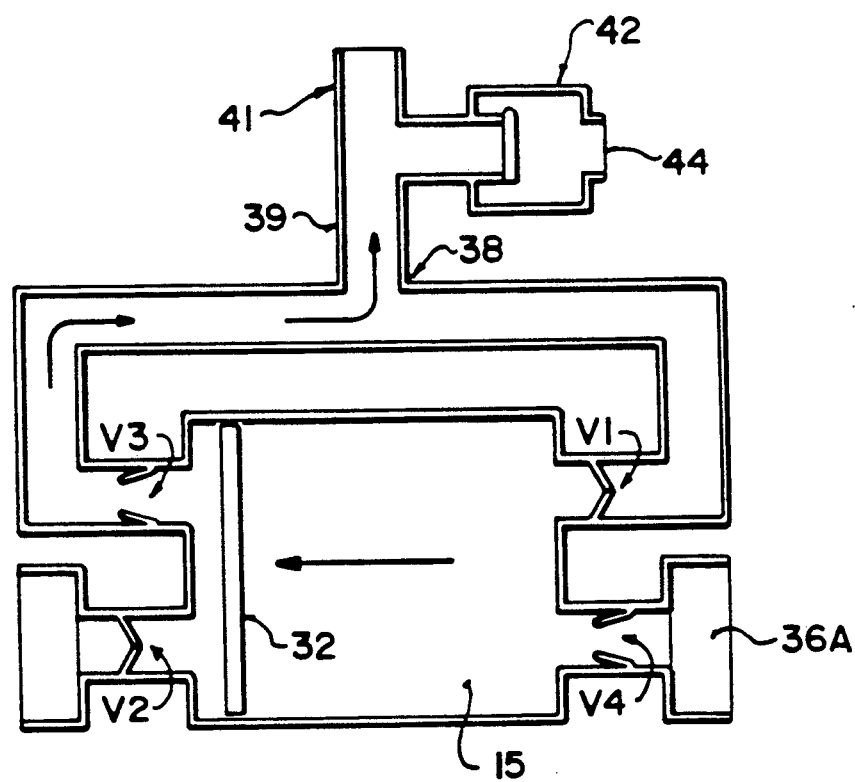

Mounted on the shaft 13 is a vane 32 which lies in an axial plane of the shaft and follows substantially the shape of the hollow chamber so that it can rotate with the shaft in a sweeping action around the hollow chamber. Around the periphery of the vane is a sealing member 33 shown in most detail in FIG. 3. The sealing member comprises a first support section 34 mounted upon an outside edge of the vane in the form of a channel which engages the edge and clamps around the edge. A sweeping or sliding or sealing flange portion 35 is mounted upon the outside edge of the sealing member to actually define a seal between the sealing member and the inside surface of the wall 16 of the chamber. Between the support portion 34 and the sealing flange 35 is provided a hollow bellows section 36 which resiliently supports the flange 35 relative to the vane 32 and provides a spring action pushing the flange against the surface 16.

The inlet duct 24 communicates with a filter 36A mounted in the outside surface of the housing 10 for receiving external air into the filter and thus along the duct 24 for injection into the chamber on one side of the dividing member 21. Similarly the inlet duct 26 communicates with a second filter 37 mounted symmetrically to the first filter on the opposed side of the housing to allow air from the exterior into the chamber on the side of the dividing member opposite to the first inlet duct.

The outlet ducts 28 and 30 communicate with a T-junction 38 connecting into a single outlet duct 39. Within the duct is mounted a humidifier schematically indicated at 40 into which air from the duct 39 enters for humidification prior to transmission along a supply line 41 to the patient along a conventional ventilator hose (not shown). A controlled valve 42 is connected to the supply line 41 at a T-fitting 43. The valve is of a flap type which is actuated by the control mechanism so that the valve is held closed during the supply of pressurized air through the supply line 41 and then is opened to allow the discharge of air during an exhaling stroke from the supply line to the exterior at an outlet 44 downstream of the valve 42.

The inlet and outlet ducts leading to the interior of the chamber extend in an axial plane through the point of connection between the wedge member or dividing member 21 and the housing and spaced longitudinally along the housing. Within each of the inlet and outlet ducts is provided a valve V1, V2, V3 and V4 which is simply of the one way valve type of any suitable design. The valves are each provided a position in the respective duct, as shown in FIG. 1, located exteriorly of the wedge member. A particularly suitable type is known as a "duck-bill" valve which operates silently and simply opens and closes on changes of air pressure or air flow in the direction required. The valve also snaps shut when air flow in the opposed direction is applied.

The motor 12 and the valve 42 are controlled by a microprocessor operated control system schematically indicated at 45. The microprocessor control is responsive to pressure transducers which detect by the slight changes in pressure the commencement of demand from the patient at the beginning of an inhaling action and the cessation of demand from the patient at the commencement of an exhaling action.

In operation the control system 45 drives the motor 12 to rotate the vane in for example initially a clockwise direction forcing air through the wedge shaped manifold which directs it through valve V1 into the humidifier and then onto the patient through the supply line 41. At the same time fresh air is drawn through the filter 37 into the expanding chamber of the cylinder through the one way valve V2.

The point when the patient feels he has enough air is detected by the pressure transducer causing the motor to be stopped momentarily and actuating the valve 42 so that the patient is allowed to exhale through the control valve 42 while the motor remains stationary.

Upon completion of exhalation, the patient control valve 42 closes and the motor is actuated by the control unit 45 to rotate in the counter clockwise direction forcing air through the manifold, through the one way valve V3 into the humidifier and onto the patient. At the same time fresh air is drawn through the one way valve V4 into the left chamber of the cylinder.

At a point suitable to the patient, the motor stops, delivering only the volume required by the patient. A full cycle is now complete. It will be appreciated therefore that the motor operates in both directions and there is no recovery or inlet stroke for the pump so that both directions of operation of the pump cause a pumping action to take place and the pump is maintained stationary during exhalation.

The control unit can arrange to move the vane slightly forwardly beyond the requirements of the patient at the termination of each stroke to ensure that there is sufficient space remaining in the return stroke to allow as much air as the patient requires. Alternatively the patient may be limited in a return stroke to the amount of air that was drawn in the first stroke. In such a case the patient will be aware that a third stroke, in the same direction as the first stroke can provide a greater volume of air by moving the vane through a greater angle from the initial rest position. In such a case, the control unit 45 acts to maintain the vane in an initial rest position or within a particular range adjacent the rest position to ensure that the vane does not gradually move wholly to one end after a large number of full cycles.

In an alternative arrangement (not shown) the pump may be driven by a motor having a drive shaft parallel to but offset from the drive shaft of the pump so that a high gear reduction can be provided between the motor and the pump. In this case a DC pulsed motor can be used of very low power with the angle of movement of the vane controlled by the number of rotations of the motor to provide a highly accurate control system.

The system described above has the following significant advantage relative to previous pump systems.

1. The oscillating vane type pump allows smaller, more compact design which is extremely important for portable applications.
2. The oscillating vane type pump has few moving parts and is inherently easier to drive which reduces friction allowing for smaller battery or longer periods away from an electrical outlet.
3. The pump is much lighter and more economic to manufacture.
4. The volume supplied to the patient is easier to control due to the simple direct drive and double acting feature.
5. The ventilator incorporates directly mounted on the housing a humidifier which again reduces the size of the system for a portable application and simplifies the air circuit to the patient.
6. The direct mounting of the filters on the housing enables the use of built in filters which can be easily changed without removing covers or requiring any tools.
7. The use of the sealing arrangement at the edge of the vane which can be extruded from a suitable plastics material such as teflon keeps friction to a minimum while allowing fairly generous dimensional tolerances in the manufacture of the vane and the housing.
8. The use of the reciprocating vane type pump provides a pump of very low inertia and very low friction so that the vane can be very quickly halted under the control of the control unit 45 to provide an exact supply of a required amount of air to the patient.
9. The very effective control of the volume of air supplied enables the device to be manufactured of a smaller size to supply a smaller quantity of air for example a maximum of two and a half liters which is suitable for the majority of users. This restricts the size of the whole unit making it more portable.
10. The use of the vane type pump enables the device to operate very quietly again making more suitable as a portable unit.

In order to further reduce the friction by acting as a lubricant, humidifying water can be directly applied into the housing of the pump to lubricate the action of the vane relative to the wall of the housing.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A ventilator for assisting the breathing of a patient comprising a pump for generating an air flow, inlet means for drawing air from an exterior supply into the pump, said inlet means including valve means for preventing expulsion of air through said inlet means from said pump, outlet means for communicating pumped air from the pump, a supply line for supplying air exiting from the pump through the outlet means to the patient, valve means connected to the supply line operable to control the supply of air from the pump to the patient in an inhaling action and to allow release of air from the patient to the exterior in an exhaling action, a drive motor for the pump, the pump comprising a drive shaft, a housing defining a chamber having a chamber surface formed by a surface of revolution about a longitudinal axis of the drive shaft, a dividing member lying in an axial plane of the chamber and extending from the shaft to the peripheral wall, the dividing member being wedge-shaped in cross section with an apex at the drive shaft and increasing in width to a base at the chamber surface, the ports being formed in side faces of the dividing member so as to face angularly around the chamber, the inlet means including a first and a second inlet duct communicating with the chamber at the dividing member with the first inlet duct having a port on one side of the dividing member and the second inlet duct having a port on an opposed side of the dividing member, the outlet means including a first and a second outlet duct communicating with the chamber at the dividing member with the first outlet duct having a port on said one side of the dividing member and the second outlet duct having a port on said opposed side of the dividing member, a vane carried by the drive shaft and extending therefrom in a substantially axial plane, sealing means for sealing an edge of the vane relative to the chamber surface such that rotation of the drive shaft in a first angular direction through an angle less than 360° causes the vane to sweep around a portion of the chamber to draw air through the first inlet duct into the chamber and to expel air from the chamber into said second outlet duct and rotation in the opposed angular direction causes the vane to sweep around a volume of the chamber to expel air through the first outlet duct to the patient, the dividing member being permanently fixed inside said chamber and said valve means comprising four valve members each mounted in a respective one of said first inlet duct, said first outlet duct, said second inlet duct and said second outlet duct at a position therein exteriorly of the dividing member.

* * * * *